United States Patent [19]

Brouwer et al.

[11] Patent Number: 5,696,151
[45] Date of Patent: Dec. 9, 1997

[54] COMPOUNDS USEFUL FOR THE INHIBITION OF THE REPLICATION OF HIV-1 AND HIV-1 MUTANTS

[75] Inventors: Walter Gerhard Brouwer, Guelph; Ewa Maria Osika, Kitchener, both of Canada; Benjamin James Pierce, Southbury, Conn.

[73] Assignees: Uniroyal Chemical Company, Inc., Middlebury, Conn.; Uniroyal Chemical Ltd./Ltee, Elmira, Canada

[21] Appl. No.: 565,493

[22] Filed: Nov. 30, 1995

[51] Int. Cl.$^6$ .......................... A61K 31/34; A61K 31/38; C07D 307/58; C07D 333/32
[52] U.S. Cl. .................. 514/448; 514/471; 549/72; 549/487
[58] Field of Search ................ 549/487, 72; 514/448, 514/471

[56] References Cited

U.S. PATENT DOCUMENTS 5,268,389  12/1993  Harrison ..................... 514/485

*Primary Examiner*—José G. Dees
*Assistant Examiner*—Mary C. Cebulak
*Attorney, Agent, or Firm*—Daniel Reitenbach

[57] ABSTRACT

Compounds of the formula

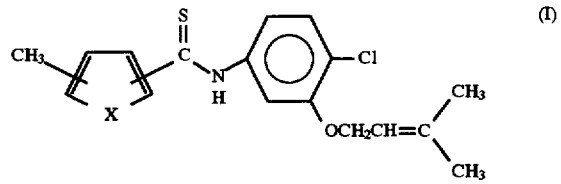

wherein X is O or S, useful for the inhibition of the replication of HIV-1 and reverse transcriptase mutants thereof, in vitro and in vivo.

12 Claims, No Drawings

COMPOUNDS USEFUL FOR THE INHIBITION OF THE REPLICATION OF HIV-1 AND HIV-1 MUTANTS

FIELD OF THE INVENTION

This invention relates to a compound useful for the inhibition of the replication of HIV-1 and HIV-1 mutant strains. More particularly, this invention relates to methylfuranyl- and methylthienyl-pentenylether derivatives which are inhibitory of the replication of wild-type HIV-1 and HIV-1 reverse transcriptase mutant strains. This invention also relates to a method for the prevention or treatment of HIV-1 infection in a patient which comprises administering to the patient an effective amount of the methylfuranyl- or methylthienyl-pentenylether derivatives.

BACKGROUND OF THE INVENTION

Various compounds have been described as inhibitors of human immunodeficiency virus type 1 (HIV-1) in vitro and are targeted at the virus-encoded reverse transcriptase (RT), e.g., nevirapine, pyridinone, TIBO, BHAP, TSAO, and quinoxaline. U.S. Pat. No. 5,268,389 describes certain thiocarboxylate ester compounds useful for inhibiting the replication of HIV. The selectivity of these compounds for HIV-1 is due to a highly specific interaction with HIV-1 RT.

The rapid emergence of HIV-1 strains resistant to several HiV-1-specific RT inhibitors in cell culture and in AIDS patients has caused concern for further development of these inhibitors in the clinic. For example, HIV-1 strains containing the 100 Leu →Ile mutation in their RT are resistant to TIBO R82913 and R82150. HIV-1 strains containing the 138 Glu →Lys mutation in their RT are resistant to TSAO derivatives. The 181 Tyr →Cys mutation in the RT of HIV-1 strains renders the mutant viruses resistant to nevirapine and pyridinone. See, e.g., Balzarini et al, J. Virology 67(9): 5353–5359 (1993) ("Balzarini I") and Balzarini et al, Virology 192: 246–253 (1993) ("Balzarini II").

Attempts have been made to combine various HIV-1 RT inhibitors to eliminate virus resistance. See, e.g., Balzarini I.

It is the purpose of this invention to provide compounds which, by themselves, can inhibit or suppress the emergence of wild-type HIV-1 and HIV-1 RT mutant strains. It is also the purpose of this invention to provide a method of preventing or treating HIV-1 infections by administration of such compounds.

SUMMARY OF THE INVENTION

This invention relates to a compound of the formula

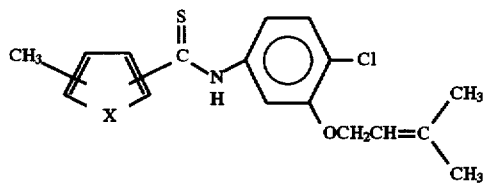

(I)

wherein X is O or S.

The compounds of this invention are useful for the inhibition of the replication of Human Immunodeficiency Virus-1 (HIV-1) and reverse transcriptase (RT) mutants thereof, in vitro and in vivo. The compounds are useful in the therapeutic or prophylactic treatment of diseases caused by HIV-1 and RT mutants thereof, such as acquired immune deficiency syndrome (AIDS).

This invention additionally relates to a pharmaceutical composition comprising a therapeutically effective amount of the compound of formula I and a pharmaceutically acceptable carrier.

This invention also relates to a method of treating HIV-1 infection in an afflicted host which comprises administering to the host a therapeutically effective amount of the compound of formula I.

DESCRIPTION OF THE INVENTION

Preferably, this invention relates to a compound of the formula

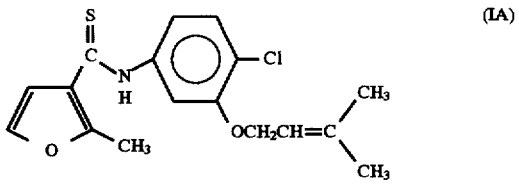

(IA)

or

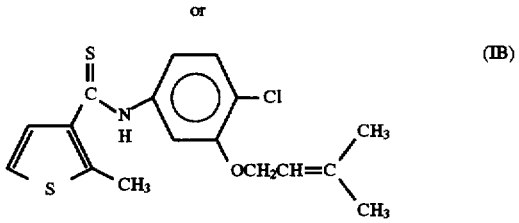

(IB)

Method of Synthesis

The compounds of this invention can be prepared by reacting an acid of the formula A—COOH wherein A is

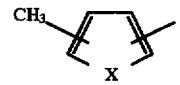

with aniline derivative of the formula

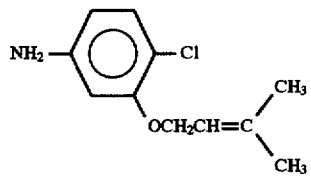

The acid, A—COOH, is first converted to its acid chloride and then treated with the aniline derivative and an acid scavenger, in a suitable solvent, to form an amide. The acid scavenger can be an organic base, such as pyridine, or an alkali metal hydroxide, carbonate or bicarbonate, such as sodium bicarbonate. Suitable solvents for this step include methylene chloride, diethyl ether, ethyl acetate, or the like. The resultant amide is then reacted with a thionylating agent such as, e.g., Lawesson's reagent or phosphorus pentasulfide, in the presence of an acid scavenger, e.g., pyridine or sodium bicarbonate, in an appropriate solvent. Heat is usually applied to complete the thionylation reaction. Suitable solvents for the thionylation reaction include toluene, xylene, DME, and the like.

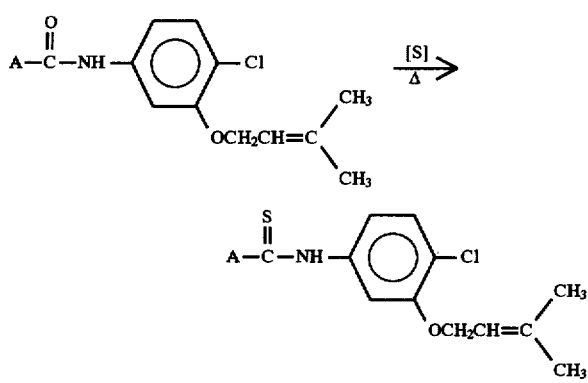

[S] = Thionylating Agent

A second method for making the compounds of this invention is the metallation of a bromo compound of the formula A—Br with n-butyl lithium, at a temperature of -75° C. to -80° C. The resultant lithium complex is then reacted with an isothiocyanate of the formula

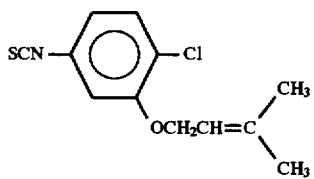

The compounds of this invention (carbothioamides) are then produced directly after acidification.

Comparative Compounds 1–117 can be prepared in a similar manner using the two methods described above. Typically, the preparation of the comparative compounds involves the formation of the amide and subsequent thionylation with Lawesson's reagent or phosphorus pentasulfide.

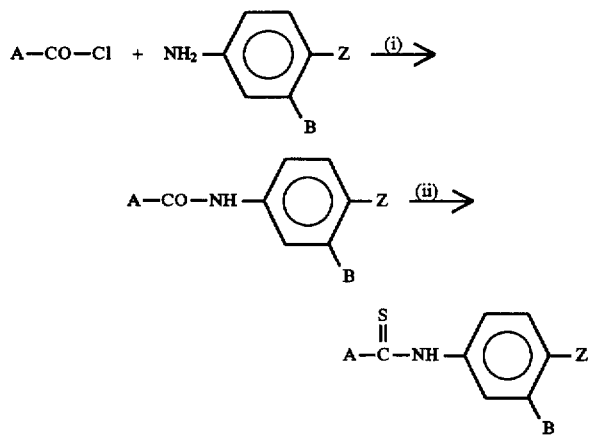

(i) Base
(ii) Lawesson's reagent or P₂S₅ with pyridine or sodium bicarbonate
A, Z and B are as defined in Table 1.

The compounds of the present invention can be administered orally, parenterally, sublingually, by inhalation spray, rectally, or topically in dosage unit formulations containing conventional non-toxic pharmaceutically acceptable carriers, adjuvants, and vehicles. Pharmaceutically acceptable carriers, adjuvants and vehicles useful in the composition of this invention can be found in standard pharmaceutical texts such as, e.g., Remington's Pharmaceutical Sciences, 16th Edition, Mack Publishing Company, Easton, Pa. (1980).

The therapeutically effective amount of the compounds of this invention that can be combined with the pharmaceutically acceptable carrier to produce a single dosage form will vary depending upon the age and condition of the host treated and the particular mode of administration. In general, the compounds of this invention are most desirably administered at a concentration level that will generally afford antivirally effective results without causing any harmful or deleterious side effects.

While the compounds of this invention can be administered as the sole active pharmaceutical agents, the compounds can also be used in combination with one or more other pharmaceutical agents which are not deleterious to the activity of the compounds of this invention or whose combination with the compounds will not have a deleterious effect on the host treated.

The following examples are provided to illustrate the present invention.

EXAMPLES

Materials and Methods
Test compounds
(A) Compound IA was prepared as follows:

(METHOD I)

Step 1

Preparation of 2-chloro-5-nitrophenol

2-Amino-5-nitrophenol (65.6 g) was added to 36% hydrochloric acid (200 mL) at 0° to 5° C. with stirring. A solution of sodium nitrite (33.25 g) in water (75 mL) was added dropwise over 1.5 hours, after which this first reaction mixture was held at this temperature for a further 1 hour. Excess nitrous acid was decomposed with sulfamic acid (1.5 g), added in portions. The first reaction mixture was then added in portions to a stirred suspension of copper (I) chloride (8.5 g) in 20% hydrochloric acid (50 mL). Considerable foaming occurred. After the addition, the resultant second reaction mixture was stirred for 1 hour. A precipitate from the second reaction mixture was then collected on a filter, washed with water and dried to give 63.2 g of brown solid. This solid was then refluxed with 1.5 g of activated carbon in methanol (500 mL) for 15 minutes; filtered through celite; and evaporated, to give 60.8 g of brown 2-chloro-5-nitrophenol.

Step 2

Preparation of 1-chloro-2-(3-methyl-2-butenyloxy)-4-nitrobenzene

A reaction mixture of 2-chloro-5-nitrophenol (50.6 g), anhydrous potassium carbonate (44.5 g), tetrabutylammonium bromide (4.7 g) and 4-bromo-2-methyl-2-butene (53.3 g, 90%) in methyl ethyl ketone (263 mL) was stirred at ambient temperature overnight. TLC of the reaction mixture showed traces of phenol remaining. Additional prenyl bromide (1 mL) was then added to the reaction mixture and stirred for 2 hours. The solvent was then removed from the reaction mixture. The residue of the reaction mixture was then treated with water and extracted into diethyl ether. The extract was washed with 2N sodium hydroxide and water, dried (MgSO₄), filtered, and evaporated, to leave a brown solid which was recrystallised from ethyl acetate/isopropyl alcohol to give 1-chloro-2-(3-methyl-2-butenyloxy)-4-nitrobenzene, 49.5 g, a beige solid, a single spot on TLC (ethyl acetate:hexane, 20:80).

Step 3

Preparation of 4-chloro-3-(3-methyl-2-butenyloxy) benzenamine

To a refluxing well-stirred suspension of iron powder (19.6 g, 100 mesh) in ethanol (60 mL), water (13.4 mL) and 36% hydrochloric acid (1.4 mL) was added 1-chloro-2-(3-methyl-2-butenyloxy)-4-nitrobenzene (24 g) in portions over 15–30 minutes. After 3 hours thin-layer chromotography (TLC) (ethyl acetate:hexane, 40:60) showed no substrate. The reaction mixture was then filtered hot and the iron oxide filter cake was washed with hot ethanol. The combined ethanol washes were evaporated to produce a residue. The residue was taken up in diethyl ether, washed with aqueous bicarbonate and water, dried ($MgSO_4$), filtered, and evaporated, to give 4-chloro-3-(3-methyl-2-butenyloxy) benzenamine, 19.8 g of light brown oil.

Step 4

Preparation of 2-methyl-3-furoyl chloride

A first reaction mixture of chloroacetaldehyde dimethylacetal (300 g), water (400 mL) and 36% hydrochloric acid (40 mL) was stirred and brought to reflux. When the first reaction mixture became homogenous, it was cooled and added to a stirred solution of ethyl acetoacetate (260 g) and pyridine (500 mL) and left stirring at ambient temperature for 72 hours, to produce a second reaction mixture. The organic layer was then separated from the second reaction mixture and the aqueous layer was diluted with water and then extracted with methylene chloride. The combined organics were washed with 2N hydrochloric acid, followed by removal of the solvent. The residue was treated with a solution of sodium hydroxide (80 g) in water (700 mL) and ethanol (100 mL), to produce a third reaction mixture. After refluxing for 1 hour the third reaction mixture was poured into ice/water and acidified with hydrochloric acid. A cream colored precipitate formed. This precipitate was collected on a filter, washed with water and dried to give 2-methyl-3-furancarboxylic acid, 180 g. 100 g of the 2-methyl-3-furancarboxylic acid was added in portions to thionyl chloride (500 mL) and refluxed for 3 hours. Excess thionyl chloride was then distilled off to produce a residue. The residue was distilled using a water pump, to give 2-methyl-3-furanylcarboxylic chloride, bp. 62° C., 100 g.

Step 5

Preparation of N-[4-chloro-3-(3-methyl-2-butenyloxy)phenyl]-2-methyl-3-furancarboxamide A first solution of 2-methyl-3-furancarboxylic chloride (13.57 g) in methylene chloride (94 mL) was stirred in an ice/salt bath. A second solution of 4-chloro-3-(3-methyl-2-butenyloxy)benzenamine (19.8 g), triethylamine (14 mL) in methylene chloride (94 mL) was added to the first solution at such a rate that the temperature was maintained at −5° C. to 0° C. When the addition was complete, the resultant reaction mixture was stirred to ambient temperature and left stirring for 15 hours. Water was added to the reaction mixture and then the organic layer separated and washed successively with water, dilute hydrochloric acid, water, aqueous sodium bicarbonate, and water. After drying ($MgSO_4$), the solvent was removed from the washed organic layer and the residue was recrystallised from isopropyl alcohol to give N-[4-chloro-3-(3-methyl-2-butenyloxy) phenyl-2-methyl-3-furancarboxamide, a white solid, 17 g. A second crop of beige crystals, 7.6 g, was also obtained.

Step 6

Preparation of N-[4-chloro-3-(3-methy-2-butenyloxy)-phenyl]-2-methyl-3-furancarbothioamide (Compound IA)

A reaction mixture of N-[4-chloro-3-(3-methyl-2-butenyloxy)phenyl]-2-methyl-3-furancarboxamide (4 g), sodium bicarbonate (7.4 g) and Lawesson's reagent (3.6 g) in toluene (168 mL) was gradually heated to 85° C. over 1 ½ hours and then held at this temperature for a further 2 ½ hours. The reaction mixture was then cooled and filtered through a plug of neutral aluminum oxide and eluted with ether:petroleum ether (1:1). Evaporation of the solvent gave the product, N-[4-chloro-3-(3-methyl-2-butenyloxy)phenyl]-2-methyl-3-furancarbothioamide, 2.6 g.

(B) Compound IB was prepared as follows:

(METHOD II)

Step 1

Preparation of 3,5-dibromo-2-methylthiophene

2-Methylthiophene (98 g) in dioxane (500 mL) was stirred while bromine (320 g) in dioxane (2L) was added dropwise over 7.5 hours and then left to stand at ambient temperature overnight. The reaction mixture was then heated to reflux for 3 hours, poured into water (4L), and extracted with ether. The ether extract was washed with aqueous bicarbonate and then water, and dried ($MgSO_4$). Evaporation left an oil which was distilled to give 3,5-dibromo-3-methylthiophene, bp. 98° C., 234.6 g.

Step 2

Preparation of 3-bromo-2-methylthiophene

Magnesium turnings (5 g) were covered with tetrahydrofuran (THF) (25 mL), and with stirring, treated with 3,5-dibromo-2-methylthiophene (5 g). An exotherm developed. The temperature of the reaction mixture was maintained at 35° C.±5° C. with cooling. Additional 3,5-dibromo-2-methylthiophene (47 g) was added dropwise to the reaction mixture while the temperature of the reaction mixture was maintained in range stated above. Towards the end of the addition, the temperature was allowed to rise to 40° C. Most of the magnesium had reacted. When the reaction exotherm ceased, the temperature of the reaction mixture was raised from 40° C. to 50° C. by external heating and maintained at 50° C. for 1 hour. The reaction mixture was then poured slowly onto vigorously-stirred ice/water/dilute hydrochloric acid, to produce a second mixture. The second mixture was extracted into ether, washed with water, dried ($MgSO_4$), and evaporated, to leave a liquid which was distilled at the water pump to give 3-bromo-2-methylthiophene, a clear liquid, bp. 62°–65° C., 32.6 g.

Step 3

Preparation of 1-chloro-2-(3-methyl-2-butenyloxy)-4-isothiocyanatobenzene

1-Chloro-2-(3-methyl-2-butenyloxy)benzenamine (19.9 g) (c.f., Method I, Step 3) was dissolved in methylene chloride (75 mL), to produce a first solution. With vigorous stirring, the first solution was then covered with ice/water (250 mL). A second solution of thiophosgene (7.3 mL) in methylene chloride (25 mL) was then added dropwise to the first solution. The resultant reaction mixture was then kept cool with an ice bath. A solid precipitated from the reaction mixture, but with time, the solid reacted further and dissolved in the methylene chloride. The reaction mixture was then allowed to come to ambient temperature by which time the reaction was complete. The organics were then separated from the reaction mixture, washed with water, dried and evaporated under reduced pressure (a caustic scrubber was used to absorb any excess thiophosgene), to produce a dark grey solid. The solid was purified by dissolving in commercial hexanes, passing the dissolved solid through a column of silica gel (minimum 3.5 cm diam.×6 cm length), and then eluting the column with hexanes. Evaporation of the hexanes solution gave a white solid, 1-chloro-2-(3-methyl-2-butenyloxy)-4-isothiocyanatobenzene, 22 g, a single spot on TLC (hexane).

Step 4

Preparation of N-[4-chloro-3-(3-methyl-2-butenyloxy)-phenyl]-2-methyl-3thiophenecarbothioamide (Compound #IB)

Under an atmosphere of nitrogen, a solution of 3-bromo-2-methylthiophene (5.5 g) in dry ether (25 mL) was cooled in an acetone/dry ice bath. n-Butyl lithium (10 mL, 2M in hexanes) was added dropwise to the solution such that the temperature of the resultant first reaction mixture did not rise by more than 2° C. After this addition, the first reaction mixture was stirred at −75° C. for 1.5 hours. 1-Chloro-2-(3-methyl-2-butenyloxy)-4-isothiocyanatobenzene (6.2 g) in dry ether (25 mL) was added dropwise to the first reaction mixture at such a rate that the temperature of the resultant second reaction mixture did not rise by more than 2° C. (1.25 hrs). After this addition, the second reaction mixture was allowed to slowly come to ambient temperature over 2 hours. The second reaction mixture was then treated with ice/water/dilute hydrochloric acid/ether. The organics were then separated from the second reaction mixture. The organics were then washed with water, dried (MgSO$_4$), and the solvents removed. A viscous yellow oil remained. A yellow solid was obtained when this oil was stirred with commercial hexanes. The yellow solid was collected on a filter, 6.2 g, and recrystallised from cyclohexane/ether to give N-[4-chloro-3-(3-methyl-2-butenyloxy)phenyl-2-methyl-3-thiophenecarbothioamide, a yellow solid, mp 118°–120° C. (uncorrected), 4.7 g.

Compounds IA and IB gave satisfactory I.R. and NMR spectra.

TABLE 1

| Cmpd. | Y | Z    | A                                     | B                                  |
|-------|---|------|---------------------------------------|------------------------------------|
| 1     | S | Cl   | 2-methyl-3-thienyl                    | —OCH$_2$CH=CHCH$_3$                |
| 2     | S | Cl   | 2-methyl-3-furanyl                    | —OCH$_2$CH—CHCH$_3$                |
| 3     | S | Cl   | 2-methyl-3-furanyl                    | —CH=N—O—C(CH$_3$)$_3$              |
| 4     | S | —OCH$_3$ | 2-methyl-3-furanyl                | —CH=N—O—CH$_3$                     |
| 5     | S | Cl   | 6-methyl-4,5-dihydro-2H-pyran-5-yl    | —CH=N—O—C(CH$_3$)$_3$              |
| 6     | S | Cl   | 2-methyl-3-furanyl                    | —S—CH$_2$CH=CHCH$_3$               |
| 7     | S | Cl   | 2-methyl-4,5-dihydro-3-furanyl        | —CH=N—O—C(CH$_3$)$_3$              |
| 8     | S | Cl   | 2-methyl-3-thienyl                    | —S—CH$_2$CH=CHCH$_3$               |
| 9     | S | Cl   | 2-methyl-3-thienyl                    | —C(O)—O—cyclohexyl                 |
| 10    | S | Cl   | 1,2-dimethyl-3-pyrrolyl               | —CH=N—O—C(CH$_3$)$_3$              |
| 11    | S | Cl   | 1-methyl-3-pyrrolyl                   | —CH=N—O—C(CH$_3$)$_3$              |
| 12    | S | Cl   | 2-methyl-3-thienyl                    | —O—CH$_2$CH$_2$CH(CH$_3$)$_2$      |
| 13    | O | Cl   | 5,6-dihydro-2-ethyl-1,4-oxathiin-3-yl | —C(O)—O—cyclohexyl                 |
| 14    | S | Cl   | 2-methyl-3-thienyl                    | —O—CH$_2$—C(O)—O—C(CH$_3$)$_3$     |
| 15    | O | Cl   | 5,6-dihydro-2-ethyl-1,4-              | —CH=N—O—C(CH$_3$)$_3$              |

TABLE 1-continued

[Structure: A-C(=Y)-N(H)-phenyl ring with Z at para position and B at meta position]

| Cmpd. | Y | Z | A | B |
|---|---|---|---|---|
| | | | oxathiin-3-yl | |
| 16 | S | Cl | 2-methyl-3-thienyl | —C(O)—O—CH(CH$_3$)$_2$ |
| 17 | S | Cl | 2-methyl-3-furanyl | —S—CH$_2$—C(O)—O—C(CH$_3$)$_3$ |
| 18 | O | Cl | 5,6-dihydro-2-methyl-1,4-oxathiin-3-yl | —CH=N—O—C(CH$_3$)$_3$ |
| 19 | S | Cl | 1,2-dimethyl-3-pyrrolyl | —O—CH$_2$CH=CHCH$_3$ |
| 20 | S | Cl | 2-methyl-3-thienyl | —S—CH$_2$—C(O)—O—C(CH$_3$)$_3$ |
| 21 | S | Cl | 2-methyl-3-thienyl | —C(O)—O—CH(CH(CH$_3$)$_2$)$_2$ |
| 22 | O | Cl | 5,6-dihydro-2-methyl-1,4-oxathiin-3-yl | —C(O)—O—CH(CH(CH$_3$)$_2$)$_2$ |
| 23 | O | Cl | 2-methyl-3-thienyl | —C(O)—O-cyclohexyl |
| 24 | O | Cl | 6-methyl-4,5-dihydro-2H-pyran-5-yl | —CH=N—O—C(CH$_3$)$_3$ |
| 25 | S | CN | 2-methyl-3-thienyl | —O—CH$_2$—C(Cl)=CH$_2$ |
| 26 | S | Cl | 2-methyl-3-furanyl | —O-cyclohexyl |
| 27 | O | Cl | 2-methyl-3-thienyl | —OCH$_2$CH=CH(CH$_3$)$_2$ |
| 28 | S | Cl | 2-methyl-3-thienyl | —O—CH$_2$-cyclopentyl |
| 29 | S | Cl | 2-methyl-3-thienyl | —OCH$_2$C(CH$_3$)$_3$ |
| 30 | O | Cl | 2-methyl-3-furanyl | —OCH$_2$CH=C(CH$_3$)$_2$ |
| 31 | O | Cl | 2-methyl-3-thienyl | —C(O)—O—CH(CH$_3$)$_2$ |
| 32 | O | Cl | 2-methyl-3-thienyl | —C(O)—O—CH(CH(CH$_3$)$_2$)$_2$ |
| 33 | O | Cl | 2-methyl-3-thienyl | —O—CH$_2$CH$_2$CH(CH$_3$)$_2$ |
| 34 | O | Cl | 2-methyl-3-thienyl | —S—CH$_2$CH=CHCH$_3$ |
| 35 | O | Cl | 2-methyl-3-furanyl | —S—CH$_2$CH=CHCH$_3$ |
| 36 | O | Cl | 2-(methylthio)-3-thienyl | —CH=N—O—C(CH$_3$)$_3$ |

TABLE 1-continued

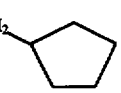

| Cmpd. | Y | Z | A | B |
|---|---|---|---|---|
| 37 | O | Cl | 2-methyl-3-furanyl | —O—CH$_2$CH$_2$CH(CH$_3$)$_2$ |
| 38 | O | Cl | 1,2-dimethyl-3-pyrrolyl | —CH=N—O—C(CH$_3$)$_3$ |
| 39 | S | Cl | 2-methyl-3-furanyl | —O—CH$_2$C(CH$_3$)$_3$ |
| 40 | O | Cl | 2-methyl-3-furanyl | —O—CH$_2$CH=CHCH$_3$ |
| 41 | O | Cl | 5,6-dihydro-2-methyl-1,4-oxathiin-3-yl | —O—CH$_2$CH$_2$CH(CH$_3$)$_2$ |
| 42 | O | Cl | 2-methyl-3-thienyl | 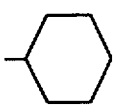 |
| 43 | O | Cl | 5,6-dihydro-2-ethyl-1,4-oxathiin-3-yl | —O—CH$_2$CH=CHCH$_3$ |
| 44 | S | Cl | 2-methyl-3-furanyl | —O—CH$_2$CH$_2$CH(CH$_3$)$_2$ |
| 45 | O | Cl | 2-methyl-3-thienyl | —O—CH$_2$CH=CHCH$_3$ |
| 46 | S | Cl | 2-methyl-3-furanyl | —O—C(O)—O—CH(CH$_3$)$_2$ |
| 47 | O | —OCH$_3$ | 2-methyl-3-furanyl | —CH=N—O—CH$_3$ |
| 48 | O | Cl | 2-methyl-3-furanyl | —C(O)—O—CH(CH$_3$)$_2$ |
| 49 | S | Cl | 2-methyl-3-furanyl | —C(O)—O—CH(CH$_3$)$_2$ |
| 50 | O | Cl | 2-methyl-3-furanyl | —C(O)—O—CH$_2$C(CH$_3$)=CH$_2$ |
| 51 | S | Cl | 2-methyl-3-furanyl | —C(O)—O—CH$_2$C(CH$_3$)=CH$_2$ |
| 52 | O | Cl | 2-methyl-3-furanyl | —CH$_2$—O—C(CH$_3$)$_3$ |
| 53 | S | Cl | 2-methyl-3-furanyl | —CH$_2$—O—C(CH$_3$)$_3$ |
| 54 | O | Cl | 2-methyl-3-furanyl | —C(O)—O—CH(CH$_3$)-cyclo-C$_3$H$_5$ |
| 55 | S | Cl | 2-methyl-3-furanyl | —C(O)—O—CH(CH$_3$)-cyclo-C$_3$H$_5$ |
| 56 | O | —OCH$_3$ | 2-methyl-3-furanyl | —CH$_2$—C(O)—O—CH(CH$_3$)$_2$ |
| 57 | S | —OCH$_3$ | 2-methyl-3-furanyl | —CH$_2$—C(O)—O—CH(CH$_3$)$_2$ |
| 58 | O | Cl | 2-methyl-3-thienyl | 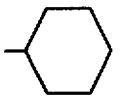 |
| 59 | S | Cl | 2-methyl-3-thienyl | 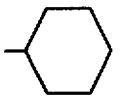 |
| 60 | O | Cl | 2-methyl-3-thienyl | —CH=N—O—C(CH$_3$)$_3$ |
| 61 | S | Cl | 2-methyl-3-thienyl | —CH=N—O—C(CH$_3$)$_3$ |
| 62 | O | Cl | Phenyl | —C(O)—O—CH(CH$_3$)$_2$ |
| 63 | S | Cl | Phenyl | —C(O)—O—CH(CH$_3$)$_2$ |

TABLE 1-continued

[Structure: A-C(=Y)-NH-phenyl with Z and B substituents]

| Cmpd. | Y | Z | A | B |
|---|---|---|---|---|
| 64 | S | Cl | 2-fluorophenyl | —C(O)—O—cyclohexyl |
| 65 | S | Cl | 2-fluorophenyl | —C(O)—O—cyclohexyl |
| 66 | O | Cl | 2-aminophenyl | —C(O)—O—CH(C$_2$H$_5$)$_2$ |
| 67 | S | Cl | 2-aminophenyl | —C(O)—O—CH(C$_2$H$_5$)$_2$ |
| 68 | O | Cl | 2-methoxyphenyl | —C(O)—O—cyclopentyl |
| 69 | S | Cl | 2-methoxyphenyl | —C(O)—O—cyclopentyl |
| 70 | O | Cl | 2-methylphenyl | —C(O)—O—cyclohexyl |
| 71 | S | Cl | 2-methylphenyl | —C(O)—O—cyclohexyl |
| 72 | S | Cl | 2-methyl-3-furanyl | —CH=N—O—CH$_3$ |
| 73 | S | —OCH$_2$ | 2-methyl-3-furanyl | —O—CH$_2$—CH=CH$_2$ |
| 74 | S | —CN | 2-methyl-3-furanyl | —O—CH$_2$—CH=CH$_2$ |
| 75 | S | —CH$_3$ | 2-methyl-3-furanyl | —C(O)—O—CH$_2$CH$_3$ |
| 76 | S | Cl | 3-methyl-2-thienyl | —O—CH$_2$—CH=CH$_2$ |
| 77 | S | —CN | 3-methyl-2-thienyl | —O—CH$_2$—CH=CH$_2$ |
| 78 | S | —OCH$_3$ | 3-methyl-2-thienyl | —O—CH$_2$—CH=CH$_2$ |
| 79 | S | Cl | 3-thienyl | —C(O)—O—cyclohexyl |
| 80 | S | Cl | 2-chlorophenyl | —C(O)—O—cyclohexyl |
| 81 | S | Cl | 2-methoxyphenyl | —C(O)—O—cyclohexyl |

TABLE 1-continued

Structure: A-C(=Y)-NH-phenyl(Z, B)

| Cmpd. | Y | Z | A | B |
|---|---|---|---|---|
| 82 | S | Cl | phenyl | −C(O)−O−cyclohexyl |
| 83 | S | Cl | 2-methyl-3-furanyl | −C(O)−O−cyclohexyl |
| 84 | S | Cl | 2-methylphenyl | −C(O)−O−cyclohexyl |
| 85 | S | Cl | 2-aminophenyl | −C(O)−O−CH(CH$_3$)$_2$ |
| 86 | S | Cl | 2-furanyl | −C(O)−O−CH(CH$_3$)$_2$ |
| 87 | S | Cl | 3-methyl-2-furanyl | −C(O)−O−CH(CH$_3$)$_2$ |
| 88 | S | Cl | 3-methyl-2-thienyl | −C(O)−O−CH(CH$_3$)$_2$ |
| 89 | S | Cl | 2-thienyl | −C(O)−O−CH(CH$_3$)$_2$ |
| 90 | S | Cl | 2-methoxyphenyl | −C(O)−O−CH(CH$_3$)$_2$ |
| 91 | S | Cl | 2-methylphenyl | −C(O)−O−CH(CH$_3$)$_2$ |
| 92 | S | Cl | 3-thienyl | −C(O)−O−CH(CH$_3$)$_2$ |
| 93 | S | Cl | phenyl | −CH=N−O−C(CH$_3$)$_3$ |
| 94 | S | Cl | 3-methyl-2-furanyl | −CH=NOCH(CH$_3$)$_2$ |
| 95 | S | Cl | 3-methyl-2-thienyl | −CH=NOCH(CH$_3$)$_2$ |
| 96 | S | Cl | phenyl | −CH=NOCH(CH$_3$)$_2$ |
| 97 | S | Cl | 2-methyl-3-furanyl | −CH=NOCH(CH$_3$)$_2$ |
| 98 | S | Cl | 2-fluorophenyl | −C(O)−O−CH(CH(CH$_3$)$_2$)$_2$ |
| 99 | S | Cl | 2-pyrrolyl | −C(O)−O−CH(CH(CH$_3$)$_2$)$_2$ |
| 100 | S | Cl | 1-methyl-2-pyrrolyl | −C(O)−O−CH(CH(CH$_3$)$_2$)$_2$ |
| 101 | S | Cl | 3-methyl-2-thienyl | −C(O)−O−CH(CH(CH$_3$)$_2$)$_2$ |
| 102 | S | Cl | 2-methyl-3-furanyl | −C(O)−O−CH(CH(CH$_3$)$_2$)$_2$ |
| 103 | S | Cl | 2-methyl-3-furanyl | −C(O)−O−CH$_2$CH(CH$_3$)$_3$ |
| 104 | S | Cl | 2-methyl-3-furanyl | −C(O)−O−CH$_2$CH=CH$_2$ |
| 105 | S | Cl | 2-methyl-3-furanyl | −C(O)−O−CH$_2$−cyclo-C$_3$H$_5$ |

TABLE 1-continued

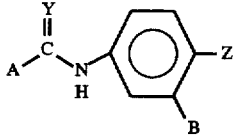

| Cmpd. | Y | Z | A | B |
|---|---|---|---|---|
| 106 | S | Cl | 2-methyl-3-furanyl | —C(O)—O—CH$_2$—CF$_3$ |
| 107 | S | Cl | 2-methyl-3-furanyl | —C(O)—O—CH (CH$_2$CH$_3$)$_2$ |
| 108 | S | Cl | 2-methyl-3-furanyl | —C(O)—O—CH$_2$CH(CH$_2$CH$_3$)$_2$ |
| 109 | S | Cl | 2-methyl-3-furanyl | —C(O)—O—cyclopentyl |
| 110 | S | Cl | 2-methyl-3-furanyl | —C(O)—O—C(CH$_3$)$_2$—CH=CH$_2$ |
| 111 | S | Cl | 2-methyl-3-furanyl | —CH=N—O—CH$_2$CH=CH$_2$ |
| 112 | S | Cl | 2-methyl-3-furanyl | —CH=N—O—CH$_2$C≡CH |
| 113 | S | Cl | 2-methyl-3-furanyl | —CH=N—O—cyclopentyl |
| 114 | S | Cl | 2-methyl-3-furanyl | —CH=N—O—C(CH$_3$)$_3$ |
| 115 | S | Cl | 2-methyl-3-furanyl | —O—CH$_2$—C(O)—O—C(CH$_3$)$_3$ |
| 116 | S | Cl | 2-methyl-3-furanyl | —S—CH$_2$—C(O)—O—CH$_2$CH$_3$ |
| 117 | S | Cl | 2-methyl-3-furanyl | —O—CH$_2$—C≡CH |

Cells and Viruses

CEM cells were obtained from the American Tissue Cell Culture Collection (Rockville, Md.). HIV-1(III$_B$) was originally obtained from the culture supernatant of persistently HIV-1-infected H9 cells and was provided by R. C. Gallo and M. Popovic (National Cancer Institute, National Institutes of Health, Bethesda, Md.). The selection and characterization of the HIV-1 RT mutant strains were done as follows: HIV-1/100-Ile ("100-Ile") was selected for resistance against TIBO R82150 as described in Balzarini et al, Virology 192: 246–253 (1993); HIV-1/103-Asn ("103-Asn") was selected for resistance against TIBO R82913 as described in Balzarini et al, Virology 192: 246–253 (1993); HIV-1/106-Ala ("106-Ala") was selected for resistance against nevirapine as described in Balzarini et al, J. Virol. 67: 5353–5359 (1993); HIV-1/Lys-138 ("Lys-138") was selected for resistance against TSAO-m$^3$T as described in Balzarini et al, Virology 192: 246–253 (1993) and Balzarini et al, Proc. Nat. Acad. Sci. USA 90: 6952–6956 (1993); HIV-1/181-Cys ("181-Cys") was selected for resistance against pyridinone L-697,661 as described in Balzarini et al, Virology 192: 246–253 (1993); and HIV-1/188-His ("188-His") was selected for resistance against HEPT as described in Balzarini et al, Mol. Pharmocol. 44: 694–701 (1993). 188-His was then further converted to HIV-1/188-Leu "188-Leu") upon further passage in cell culture in the absence of the HEPT.

Antiviral activity of the test compounds in cell cultures

CEM cells were suspended at ≈300,000 cells per ml of culture medium and infected with approximately 100 CCID$_{50}$ (CCID$_{50}$ being the 50% cell culture infective dose) of HIV-1(III$_B$) or one of the HIV-1 RT mutant strains described above. Then 100 µl of the infected cell suspensions was added to 200 µl microtiter plate wells containing 100 µl of appropriate serial (5-fold) dilutions of the test compounds. The inhibitory effect of the test compounds on HIV-1 induced syncytium formation in CEM cells was examined microscopically on day 4 post infection. The 50% effective concentration (EC$_{50}$) was defined as the test compound concentration that inhibits syncytium formation in the HIV-1-infected cell cultures by 50%.

Results

As seen below in Tables 2A and 2B, compounds IA and IB had extremely low, and virtually similar EC$_{50}$ values against HIV-1(III$_B$)(designated as "WT" in Tables 2A and 2B) and the HIV-1 RT mutants. The EC$_{50}$ values of these two compounds against the HIV-1 RT mutant strains were as low as 0.003 to 0.011 µg/ml. Such outstanding activity against the HIV-1 RT mutant strains was surprising and unexpected when compared to the EC$_{50}$ values of Comparative Examples 1–117 against the HIV-1 RT mutant strains. Since the compounds of this invention effectively suppress wild-type HIV-1 as well as the HIV-1 RT mutant virus strains, they would also be useful to inhibit HIV-1 RT mutant strains containing more than one of the mutations.

TABLE 2A

| | Antiviral Activity[c] | | | | | | | |
|---|---|---|---|---|---|---|---|---|
| | $EC_{50}$ (μg/ml)[a] | | | | | | | $CC_{50}$ |
| Cmpd. | WT | 100-Ile | 103-Asn | 106-Ala | 138-Lys | 181-Cys | 188-Leu | (μg/ml)[b] |
| IA | 0.003 | 0.003 | 0.006 | 0.005 | 0.005 | 0.011 | 0.50 | >100 |
| IB | 0.003 | 0.004 | 0.004 | 0.005 | 0.005 | 0.005 | 0.60 | 5.8 |

[a]50% effective concentration (i.e., compound concentration required to inhibit virus-induced cytopathicity by 50%)
[b]50% cytostatic concentration (i.e., compound concentration required to inhibit CEM cell proliferation by 50%)
[c]Data are the averages of 2 to 3 independent experiments

TABLE 2B

| | Antiviral Activity of Comparative Compounds[c] | | | | | | | |
|---|---|---|---|---|---|---|---|---|
| | $EC_{50}$ (μg/ml)[a] | | | | | | | $CC_{50}$ |
| Cmpd. | WT | 100-Ile | 103-Asn | 106-Ala | 138-Lys | 181-Cys | 188-Leu | (μg/ml)[b] |
| 1 | 0.0055 | 0.048 | 0.048 | 0.023 | 0.018 | 0.03 | 0.65 | 5.9 |
| 2 | 0.006 | 0.048 | 0.023 | 0.04 | 0.018 | 0.075 | 0.65 | 9.0 |
| 3 | 0.0065 | 0.057 | 0.23 | 0.03 | 0.045 | 0.08 | 0.91 | 5.8 |
| 4 | 0.007 | 0.22 | 0.4 | 0.22 | 0.039 | 0.59 | 0.93 | >100 |
| 5 | 0.013 | 0.055 | 0.08 | 0.025 | 0.04 | 0.025 | >2 | 10 |
| 6 | 0.0041 | 0.037 | 0.03 | 0.018 | 0.03 | 0.045 | 1.0 | 4.7 |
| 7 | 0.0065 | 0.055 | 0.058 | 0.03 | 0.04 | 0.045 | 1.2 | 11 |
| 8 | 0.0055 | 0.032 | 0.023 | 0.023 | 0.025 | 0.025 | >2.0 | 5.1 |
| 9 | 0.0032 | 0.057 | 0.13 | 0.03 | 0.02 | 0.032 | ≧2 | 6.0 |
| 10 | 0.02 | 0.65 | 1.27 | 0.23 | 0.09 | 0.033 | >2 | 6.5 |
| 11 | 0.029 | 0.13 | 0.17 | 0.1 | 0.13 | 0.045 | >2 | 13 |
| 12 | 0.007 | 0.035 | 0.035 | 0.08 | 0.035 | 0.07 | >2.0 | >100 |
| 13 | 0.08 | 0.26 | 0.38 | 0.17 | 0.25 | 0.07 | ≧2 | 11.4 |
| 14 | 0.067 | 0.16 | 0.12 | 0.1 | 0.24 | 0.087 | >2 | 2.1 |
| 15 | 0.03 | 0.06 | 0.065 | 0.06 | 0.07 | 0.09 | >2 | 11.4 |
| 16 | 0.0041 | 0.15 | 0.33 | 0.077 | 0.03 | 0.1 | >2.0 | 5.9 |
| 17 | 0.22 | 0.49 | 0.73 | 0.3 | 0.18 | 0.45 | ≧2 | 7.0 |
| 18 | 0.014 | 0.33 | 0.33 | 0.15 | 0.22 | 0.13 | >2 | 8.5 |
| 19 | 0.17 | 0.85 | ≧2.0 | 0.4 | 0.6 | 0.13 | >2 | 5.2 |
| 20 | 0.13 | 0.34 | 0.44 | 0.15 | 0.43 | 0.14 | >2 | 5.4 |
| 21 | 0.008 | 0.3 | 0.61 | 0.23 | 0.11 | 0.17 | >2 | 6.0 |
| 22 | 0.08 | 0.48 | 0.65 | 0.26 | 0.55 | 0.18 | >2 | 5.8 |
| 23 | 0.03 | 0.7 | ≧2.0 | 0.22 | 0.73 | 0.27 | >2 | 5.8 |
| 24 | 0.13 | 0.48 | 0.6 | 0.5 | 0.5 | 0.33 | >2 | 9.7 |
| 25 | 0.03 | 0.2 | 0.4 | 0.2 | 0.13 | 0.44 | >2 | 3.3 |
| 26 | 0.033 | 0.33 | 0.33 | 0.09 | 0.50 | ≧2.0 | >2 | 5.3 |
| 27 | 0.01 | 0.36 | 0.5 | 0.11 | 0.15 | 0.46 | >2 | 6.0 |
| 28 | 0.029 | 0.22 | 0.33 | 0.23 | 0.11 | 0.5 | >2 | 4.3 |
| 29 | 0.14 | 0.5 | 0.43 | 0.5 | 0.05 | 0.55 | >2 | 6.2 |
| 30 | 0.015 | 1.27 | 1.67 | 0.34 | 0.23 | 0.65 | >2 | >100 |
| 31 | 0.09 | ≧2.0 | ≧2.0 | 0.6 | 0.93 | 0.73 | >2 | 5.5 |
| 32 | 0.16 | ≧2.0 | ≧2.0 | ≧2.0 | ≧2.0 | 0.95 | >2 | 4.1 |
| 33 | 0.063 | 0.95 | 1.0 | 0.65 | 0.62 | 1.07 | >2 | 7.0 |
| 34 | 0.08 | 0.65 | 0.8 | 0.28 | 0.5 | 1.2 | >2 | 4.8 |
| 35 | 0.16 | 1.5 | 0.55 | 0.8 | 0.7 | 1.6 | >2 | 5.9 |
| 36 | 0.18 | 1.23 | 1.2 | 0.85 | 0.85 | 1.6 | >2 | 7.8 |
| 37 | 0.16 | ≧2.0 | ≧2.0 | 1.3 | 1.25 | 1.73 | >2 | 5.0 |
| 38 | 0.08 | ≧2.0 | ≧2.0 | 0.7 | ≧2.0 | >2 | >2 | 5.5 |
| 39 | 0.15 | 1.4 | 0.7 | >2 | 0.5 | ≧2.0 | >2 | 4.1 |
| 40 | 0.24 | 1.4 | ≧2.0 | >2 | 1.2 | >2 | >2 | 5.8 |
| 41 | 0.28 | ≧2.0 | ≧2.0 | ≧2.0 | ≧2.0 | ≧2.0 | >2 | >100 |
| 42 | 0.36 | ≧2.0 | ≧2.0 | ≧2.0 | ≧2.0 | ≧2.0 | >2 | 5.0 |
| 43 | 0.65 | 1.2 | 1.3 | 4.5 | 1.3 | >2 | >2 | 11 |
| 44 | 0.0073 | 0.035 | 0.08 | 0.06 | 0.03 | 0.08 | >10 | >100 |
| 45 | 0.15 | 0.6 | 0.95 | 0.85 | 0.65 | 0.5 | >10.0 | 87 |
| 46 | 0.37 | 4.5 | 4.0 | 3.0 | 0.6 | 5.5 | ≧2 | 25 |
| 47 | 0.23 | ≧10 | ≧10 | ≧10 | ≧10 | ≧10 | ≧10 | >100 |
| 48 | 0.45 | 6.5 | — | 6.5 | 3.5 | 6.0 | — | 3.8 |
| 49 | 0.007 | 0.6 | — | 0.6 | 0.6 | 0.2 | — | 5.2 |
| 50 | 0.15 | 5.0 | — | 1.0 | 1.0 | 1.9 | — | 3.7 |
| 51 | 0.006 | 0.8 | — | 0.03 | 0.03 | 0.10 | — | 6.7 |
| 52 | 0.70 | 8.5 | — | 5.5 | 4.0 | ≧10 | — | 6.2 |
| 53 | 0.03 | 0.85 | — | 0.29 | 0.08 | 0.55 | — | 18 |
| 54 | 0.6 | >10 | — | 5.0 | >10 | 1.0 | — | 44 |
| 55 | 0.009 | 0.65 | — | 0.08 | 0.18 | 0.11 | — | 17 |

TABLE 2B-continued

Antiviral Activity of Comparative Compounds[c]

| Cmpd. | EC$_{50}$ (µg/ml)[a] | | | | | | CC$_{50}$ (µg/ml)[b] |
|---|---|---|---|---|---|---|---|
| | WT | 100-Ile | 103-Asn | 106-Ala | 138-Lys | 181-Cys | 188-Leu | |
| 56 | 0.7 | >10 | — | 6.5 | ≧10 | >10 | — | 52 |
| 57 | 0.009 | 1.3 | — | 0.2 | 0.08 | 0.50 | — | >100 |
| 58 | 0.19 | 5.5 | — | 7.0 | 6.0 | 5.0 | — | 6.5 |
| 59 | 0.09 | 0.65 | — | 0.60 | 0.40 | 0.35 | — | 15 |
| 60 | 0.23 | 4.5 | — | 1.6 | 1.57 | 3.0 | — | 14 |
| 61 | 0.01 | 0.2 | — | 0.2 | 0.05 | 0.2 | — | 12 |
| 62 | 0.4 | 3.5 | — | 5.0 | 5.0 | 5.5 | — | 6.2 |
| 63 | 0.05 | 4.5 | — | 5.0 | 2.2 | 5.0 | — | 4.3 |
| 64 | 0.6 | ≧10 | — | 2.0 | 4.0 | 5.0 | — | 33 |
| 65 | 0.04 | 0.3 | — | 0.26 | 0.09 | 0.25 | — | 19 |
| 66 | 0.6 | >10 | — | 9.0 | >10 | ≧10 | — | 25 |
| 67 | 0.75 | ≧10 | — | ≧10 | 5.5 | >10 | — | 29 |
| 68 | 0.45 | 5.0 | — | 8.5 | 5.5 | 8.5 | — | >100 |
| 69 | 0.04 | 0.65 | — | 0.65 | 0.55 | 3.5 | — | 10 |
| 70 | 0.19 | 2.5 | — | 6.5 | 5.5 | 2.5 | — | 5.2 |
| 71 | 0.049 | 0.6 | — | 3.0 | 3.0 | 1.6 | — | 4.0 |
| 72 | 0.03 | 2.3 | — | 0.5 | 0.085 | 1.6 | — | 24 |
| 73 | 0.017 | 2.9 | — | 0.80 | 0.09 | 0.85 | — | >100 |
| 74 | 0.015 | 6.0 | — | 0.45 | 0.09 | 3.0 | — | >100 |
| 75 | 0.009 | 0.9 | — | 0.7 | 0.35 | 0.6 | — | 16 |
| 76 | 0.035 | 2.7 | — | ≧1 | 0.73 | >1 | — | 5.3 |
| 77 | 0.045 | ≧1 | — | ≧1 | 0.55 | >1 | — | 3.6 |
| 78 | 0.045 | 5.0 | — | 2.0 | 1.13 | 3.3 | — | 7.1 |
| 79 | 0.03 | 0.85 | — | 0.07 | 0.07 | 0.08 | — | 4.1 |
| 80 | 0.50 | 4.0 | — | 5.0 | 4.0 | 3.0 | — | 8.3 |
| 81 | 0.04 | 0.7 | — | 0.65 | 0.6 | 4.5 | — | 12 |
| 82 | 0.03 | 2.0 | — | 1.0 | 0.55 | 0.8 | — | 5.2 |
| 83 | 0.004 | 0.17 | — | 0.057 | 0.035 | 0.07 | — | 9.7 |
| 84 | 0.049 | 0.6 | — | 3.0 | 3.0 | 1.6 | — | 4.0 |
| 85 | 0.5 | 6.0 | — | 7.5 | 5.5 | 5.3 | — | 6.7 |
| 86 | 0.1 | 5.0 | — | 5.0 | 4.0 | 5.0 | — | 7.4 |
| 87 | 0.02 | 3.0 | — | 1.0 | 0.55 | 0.53 | — | 15 |
| 88 | 0.01 | 0.7 | — | 0.6 | 0.3 | 0.27 | — | 5.2 |
| 89 | 0.09 | 3.0 | — | 4.0 | 1.9 | 4.0 | — | 4.9 |
| 90 | 0.19 | 3.5 | — | 6.0 | 0.7 | 5.5 | — | 27 |
| 91 | 0.45 | 4.5 | — | 8.5 | 5.0 | 7.5 | — | 5.8 |
| 92 | 0.02 | 0.4 | — | 0.75 | 0.50 | 0.37 | — | 4.3 |
| 93 | 0.03 | 2.0 | — | 0.10 | 0.08 | 0.7 | — | 9.7 |
| 94 | 0.01 | 0.75 | — | 0.50 | 0.15 | 0.6 | — | 3.1 |
| 95 | 0.008 | 0.65 | — | 0.08 | 0.16 | 0.5 | — | 13 |
| 96 | 0.05 | >1 | — | 0.75 | 0.17 | >1 | — | 9.0 |
| 97 | 0.009 | 3.5 | — | ≧4 | 2.0 | 3.3 | — | 3.3 |
| 98 | 0.06 | >1 | — | 0.85 | 0.7 | >1 | — | 7.5 |
| 99 | 0.10 | >1 | — | >10 | >10 | >10 | — | >100 |
| 100 | 0.03 | 4.0 | — | 0.8 | 0.4 | 0.65 | — | >100 |
| 101 | 0.045 | 3.0 | — | 0.2 | 0.33 | 0.55 | — | ≧100 |
| 102 | 0.03 | 0.85 | — | 0.85 | 0.08 | 0.65 | — | 3.7 |
| 103 | 0.01 | 0.19 | — | 0.075 | 0.06 | 0.07 | — | 8.5 |
| 104 | 0.01 | 0.65 | — | 0.4 | 0.2 | 0.37 | — | 11 |
| 105 | 0.015 | 0.4 | — | 0.2 | 0.085 | 0.07 | — | 6.7 |
| 106 | 0.007 | 0.5 | — | 0.08 | 0.065 | 0.085 | — | >100 |
| 107 | 0.04 | 0.6 | — | 0.3 | 0.15 | 0.3 | — | 16 |
| 108 | 0.007 | 0.27 | — | 0.08 | 0.07 | 0.08 | — | 7.0 |
| 109 | 0.005 | 0.17 | — | 0.04 | 0.035 | 0.045 | — | 4.3 |
| 110 | 0.04 | 4.0 | — | 0.2 | 0.1 | 0.5 | — | 25 |
| 111 | 0.007 | 0.5 | — | 0.085 | 0.077 | 0.3 | — | 12 |
| 112 | 0.025 | 0.75 | — | 0.35 | 0.5 | 0.8 | — | 10 |
| 113 | 0.023 | 0.27 | — | 0.085 | 0.15 | 0.13 | — | 5.4 |
| 114 | 0.05 | 0.085 | — | 0.13 | 0.075 | 0.075 | — | 5.8 |
| 115 | 0.29 | 0.65 | — | 0.2 | 0.77 | 0.5 | — | 4.3 |
| 116 | 0.085 | 1.8 | — | 5.5 | 0.6 | 2.0 | — | ≧100 |
| 117 | 0.06 | 5.0 | — | 0.75 | 0.35 | 4.0 | — | 18 |

[a]50% effective concentration (i.e. compound concentration required to inhibit virus-induced cytopathicity by 50%)
[b]50% cytostatic concentration (i.e. compound concentration required to inhibit CEM cell proliferation by 50%)
[c]Data are the averages of 2 to 3 independent experiments

What is claimed is:

1. A compound of the formula

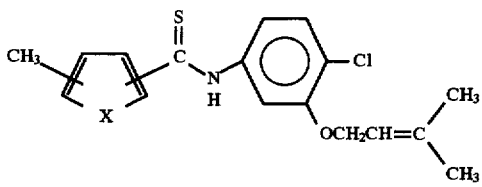

wherein X is O or S.

2. A compound as recited in claim 1 having the formula

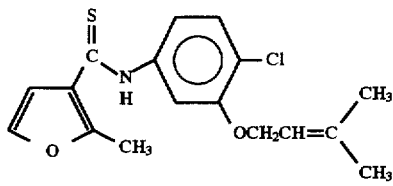

3. A compound having the formula

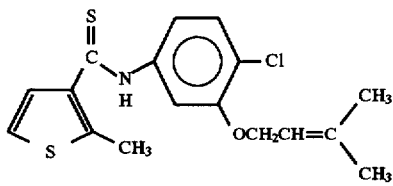

4. A pharmaceutical composition useful for treating wild-type HIV-1 or HIV-1 reverse transcriptase mutant infection in an afflicated host, comprising a therapeutically effective amount of the compound as recited in claim 1 and a pharmaceutically acceptable carrier.

5. A pharmaceutical composition useful for treating wild-type HIV-1 or HIV-1 reverse transcriptase mutant infection in an afflicated host, comprising a therapeutically effective amount of the compound as recited in claim 2 and a pharmaceutically acceptable carrier.

6. A pharmaceutical composition comprising useful for treating wild-type HIV-1 or HIV-1 reverse transcriptase mutant infection, in an afflicated host, a therapeutically effective mount of the compound as recited in claim 3 and a pharmaceutically acceptable carrier.

7. A method of treating wild-type HIV-1 or HIV-1 reverse transcriptase mutant infection in an afflicted host which comprises administering to the host a therapeutically effective amount of the compound as recited in claim 1.

8. A method of treating wild-type HIV-1 or HIV-1 reverse transcriptase mutant infection in an afflicted host which comprises administering to the host a therapeutically effective amount of the compound as recited in claim 2.

9. A method of treating wild-type HIV-1 or HIV-1 reverse transcriptase mutant infection in an afflicted host which comprises administering to the host a therapeutically effective amount of the compound as recited in claim 3.

10. A method of inhibiting the replication of HIV-1 or HIV-1 reverse transcriptase mutants which comprises contacting the HIV-1 or HIV-1 reverse transcriptase mutant with an effective amount of a compound as recited in claim 1.

11. A method of inhibiting the replication of HIV-1 or HIV-1 reverse transcriptase mutants which comprises contacting the HIV-1 or HIV-1 reverse transcriptase mutant with an effective amount of a compound as recited in claim 2.

12. A method of inhibiting the replication of HIV-1 or HIV-1 reverse transcriptase mutants which comprises contacting the HIV-1 or HIV-1 reverse transcriptase mutant with an effective amount of a compound as recited in claim 3.

* * * * *